United States Patent [19]

Kaeding

[11] 4,049,573
[45] Sept. 20, 1977

[54] ZEOLITE CATALYST CONTAINING OXIDE OF BORON OR MAGNESIUM

[75] Inventor: Warren W. Kaeding, Westfield, N.J.

[73] Assignee: Mobil Oil Corporation, New York, N.Y.

[21] Appl. No.: 655,330

[22] Filed: Feb. 5, 1976

[51] Int. Cl.² ............... B01J 21/02; B01J 27/14; B01J 29/06
[52] U.S. Cl. .................... 252/432; 252/437; 252/455 Z
[58] Field of Search ............ 252/432, 437, 455 Z; 260/681, 682, 683.44, 683.66

[56] References Cited

U.S. PATENT DOCUMENTS

| | | | |
|---|---|---|---|
| 3,405,074 | 10/1968 | Mattox | 252/455 Z |
| 3,894,104 | 7/1975 | Chang et al. | 260/682 X |
| 3,954,670 | 5/1976 | Pine | 252/432 |
| 3,972,832 | 8/1976 | Butter et al. | 252/437 |

Primary Examiner—Carl F. Dees
Attorney, Agent, or Firm—Charles A. Huggett; Raymond W. Barclay

[57] ABSTRACT

A catalytic process is provided for converting lower monohydric alcohols and their ethers, especially methanol and dimethyl ethers, to a hydrocarbon mixture rich in $C_2$-$C_3$ olefins and mononuclear aromatics with high selectivity for para-xylene production by contact, under conversion conditions, with a catalyst comprising a crystalline aluminosilicate zeolite, said zeolite having a silica to alumina ratio of at least about 12 and a constraint index, as hereinafter defined, within the approximate range of 1 to 12, said catalyst having been modified by the addition thereto of a minor proportion of an oxide of boron or magnesium either alone or in combination, or in further combination with an oxide of phosphorus.

10 Claims, No Drawings

ZEOLITE CATALYST CONTAINING OXIDE OF BORON OR MAGNESIUM

SUMMARY OF THE INVENTION

In accordance with the present invention, there has been discovered a process which can simultaneously produce both valuable light olefinic hydrocarbons and mononuclear aromatics with high selectivity for para-xylene formation, or light olefins primarily by selection of temperature conditions. The present process involves conversion of lower monohydric alcohols having up to four carbon atoms, their ether derivatives or mixtures of any of these by contact at elevated temperatures with a catalyst comprising a crystalline alumino-silicate zeolite, which zeolite has a silica to alumina ratio of at least about 12 and a constraint index within the approximate range of 1 to 12, said catalyst having combined therewith boron oxide, magnesium oxide, either alone or in combination, or in further combination with phosphorus oxide. Compounds which modify the active specified crystalline aluminosilicate zeolite in accordance with the present invention include boron oxide, magnesium oxide, a mixture of boron oxide and magnesium oxide, boron oxide and phosphorus oxide, magnesium oxide and phosphorus oxide or boron oxide, magnesium oxide and phosphorus oxide. The amount of such added oxide or oxide combinations is generally at least about 0.25 percent by weight of the resulting product.

The alcohols may be manufactured from synthesis gas, i.e. a mixture of CO and $H_2$, from coal or they may be produced by fermentation or they may be manufactured from petroleum fractions in excess supply. The aromatic hydrocarbon produced may be used to blend with gasoline, or they may be separated and used as petrochemicals or as solvents. Thus, in one aspect, the present invention affords a novel means for producing hydrocarbon petrochemicals and fuels.

The present process comprises conversion of the aforenoted alcohols and/or ethers in the presence of the specified catalyst at a temperature between about 250° C and about 700° C and preferably between about 275° C and about 500° C at a pressure between about 0.2 and about 30 atmospheres utilizing a feed weight hourly space velocity (WHSV) between about 0.1 and about 20. The latter WHSV is based upon the weight of catalyst composition, i.e. total weight of active catalyst and binder therefor. The effluent is separated and distilled to remove the desired products of light olefinic hydrocarbons and para-xylene. Any unreacted product may be recycled for further reaction.

DESCRIPTION OF SPECIFIC EMBODIMENTS

It is contemplated that any monohydric alcohol having from 1 to 4 carbon atoms or ethers derived from these alcohols may be used as feed to the process of this invention. Thus, methanol, ethanol, n-propanol, isopropanol, n-butanol, sec-butanol and isobutanol may be used either alone or in admixture with ethers derived from such alcohols. Likewise, the noted ethers, e.g. methyl-ethyl ether may be similarly used. Particularly preferred feeds are methanol, dimethyl ether and mixtures thereof.

In accordance with the present invention, such feed is brought into contact, under conversion conditions, with a bed comprising particle-form catalyst containing a crystalline aluminosilicate zeolite having: (1) a silica to alumina ratio of at least about 12, (2) a constraint index within the approximate range of 1 to 12 and (3) which catalyst has been modified with at least about 0.25 weight percent of an oxide of boron or magnesium, either alone or in combination or in further combination with an oxide of phosphorus.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalyst having higher ratios of at least about 30. Such catalyst, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section then normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other case, that may be operative.

Rather then attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index aproximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F to 950° F, with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F to 950° F, the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Patent 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)\ M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to a about 50.

The synthetic ZSM-38 zeolite possesses a definite distinguishing crystalline structure whose X-ray diffraction pattern shows substantially the significant lines set forth in Table I. It is observed that his X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides falling within the following ranges:

| R+ | Broad | Preferred |
|---|---|---|
| R+ + M+ | 0.2–1.0 | 0.3–0.9 |
| OH−/SiO$_2$ | 0.05–0.5 | 0.07–0.49 |
| H$_2$O/OH− | 41–500 | 100–250 |
| SiO$_2$/Al$_2$O$_3$ | 8.8–200 | 12–60 | wherein R is an organic nitrogen-containing cation derived from a 2-(hydroxyalkyl) trialkyammonium compound and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° C to about 400° C for a period of time of from about 6 hours to about 100 days. A more preferred temperature range is from about 150° C to about 400° C with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F for from about 8 to 24 hours.

ZSM-35 is more particularly described in U.S. Application Ser. No. 528,061, filed Nov. 29, 1974. This zeolite can be identified, in terms of mole ratios of oxides and in the anhydrous state, as follows:

(0.3–2.5)R$_2$O: (0–0.8)M$_2$O : Al$_2$O$_3$ : > 8 SiO$_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R$_2$O : (0.0.6) M$_2$O : Al$_2$O$_3$ : xSiO$_2$ wherein R is an organic nitrogen-containing cation derived from ethylenediamine or pyrrolidine, M is an alkali metal, especially sodium and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio N-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO$_2$ | 0.05–0.5 | 0.07–0.49 |
| H$_2$O/OH 116 | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zealite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° C to about 400° C for a period of time of from about 6 hours to about 100 days. A more preferred temperature range is from about 150° C to about 400° C with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F, for from about 8 to 24 hours.

The specific zeolites described, when prepared in the presence of organic cations, are catalytically inactive, possible because the intracrystalline free space is occupied by organic cations from the forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Group I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired becuase they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | | Framework Density | |
|---|---|---|---|---|
| Ferrierite | 0.28 | cc/cc | 1.76 | g/cc |
| Mordenite | .28 | | 1.7 | |
| ZSM-5, -11 | .29 | | 1.79 | |
| Dachiardite | .32 | | 1.72 | |
| L | .32 | | 1.61 | |
| Clinoptilolite | .34 | | 1.71 | |
| Laumontite | .34 | | 1.77 | |
| ZSM-4 (Omega) | .38 | | 1.65 | |
| Heulandite | .39 | | 1.69 | |
| P | .41 | | 1.57 | |
| Offretite | .40 | | 1.55 | |
| Levynite | .40 | | 1.54 | |
| Erionite | .35 | | 1.51 | |
| Gmelinite | .44 | | 1.46 | |
| Chabazite | .47 | | 1.45 | |
| A | .5 | | 1.3 | |
| Y | .48 | | 1.27 | |

When synthesized in the alkali metal form, the zeolite is conveniently converted to the hydrogen form, generally by intermediate formation of the ammonium form as a result of ammonium ion exchange and calcination of the ammonium form to yield the hydrogen form. In general, it is contemplated that more than 50 percent and preferably more than 75 percent of the cationic sites of the crystalline aluminosilicate zeolite, above described, will be occupied by hydrogen ions. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen, are then contacted with a boron and/or magnesium compound.

Representative boron-containing compounds include boric acid, trimethylborate, boron oxide, boron sulfide, boron hydride, butylboron dimethoxide, butylboric acid, dimethylboric anhydride, hexamethylborazine, phenyl boric acid, triethylborane, diborane, alkylborate and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating compound is effected by contacting the zeolite with such compound. Where the treating compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the treating compound is, for example, trimethylborate, a hydrocarbon solvent such as n-octane may be employed. The treating compound may be used without a solvent, i.e. may be used as a neat liquid. Where the treating compound is in the gaseous phase, such as where gaseous diborane is employed, the treating compound can be used by itself or can be used in admixture with a gaseous diluent relatively inert to the treating compound and the zeolite such as helium or nitrogen or with an organic solvent, such as octane or toluene.

Prior to reacting the zeolite with the treating compound, the zeolite may be dried. Drying can be effected in the presence of air. Elevated temperatures may be employed. However, the temperature should not be such that the crystal structure of the zeolite is destroyed.

Heating of the boron or magnesium compound impregnated catalyst subsequent to preparation and prior to use is also preferred. The heating can be carried out in the presence of oxygen, for example, air. Heating can be at a temperature of about 150° C. However, higher temperatures, i.e. up to about 500° C are preferred. Heating is generally carried out for 3-5 hours but may be extended to 24 hours or longer. While heating temperatures above about 500° C can be employed, they are not necessary. At temperatures of about 1000° C, the crystal structure of the zeolite tends to deteriorate. After heating in air at elevated temperatures, the oxide form of the impregnating reagent is present.

The amount of boron and/or magnesium oxide incorporated in the calcined zeolite should be at least about 0.25 percent by weight. However, it is preferred that the amount of boron and/or magnesium oxide in the zeolite be at least about 1 percent by weight when the same is combined with a binder, e.g. 35 weight percent of alumina. The amount of boron and/or magnesium oxide can be as high as about 25 percent by weight or more depending on the amount and type of binder present. Preferably, the amount of such oxide added to the zeolite is between about 1 and about 15 percent by weight. When the zeolite has both boron oxide and magnesium oxide, combined therewith, the amount of boron oxide is desirably in the approximate range of 0.25 to 5 percent by weight and the magnesium oxide content within the approximate range of 2 to 15 percent by weight.

The amount of boron and/or magnesium oxide incorporated with the zeolite by reaction with the treating solution and subsequent calcination in air will depend upon several factors. One of these is the reaction time, i.e. the time that the zeolite and the boron and/or magnesium-containing source are maintained in contact with each other. With greater reaction times, all other factors being equal, a greater amount of the metal oxide is incorporated with the zeolite. Other factors upon which the amount of metal oxide incorporated with the zeolite is dependent include reaction temperature, concentration of the treating compound in the reaction mixture, the degree to which the zeolite has been dried prior to reaction with the treating compound, the conditions of drying of the zeolite after reaction of the zeolite with the treating compound, and the amount and type of binder incorporated with the zeolite.

The zeolite containing boron oxide and/or magnesium oxide may have further combined therewith an oxide of phosphorus. In such instance, the amount of phosphorus oxide is generally between about 0.25 and about 10 and preferably between about 0.5 and about 5 weight percent. To effect combination of the boron oxide and/or magnesium oxide modified zeolite with phosphorus oxide, such zeolite is contacted with a phosphorus-containing compound either in the form of a solution in water or other suitable solvent or in the gaseous phase. Representative phosphorus-containing compounds include derivatives of groups represented by $PX_3$, $RPX_2$, $R_2PX$, $R_3P$, $R_3P=O$, $RPO_2$, $RP(O)(OX)_2$, $R_2P(O)OX$, $RP(OX)_2$, $ROP(OX)_2$, and $(RO)_2POP(OR)_2$, where R is an alkyl or phenyl radical and X is hydrogen, R, or halide. These compounds include primary, $RPH_2$, secondary, $R_2PH$, and tertiary, $R_3P$, phosphines such as butyl phosphine; the tertiary phosphine oxides, $R_3PO$, such as tributylphosphine oxide; the primary, $RP(O)(OX)_2$, and secondary, $R_2P(O)OX$, phosphonic acids such as benzene phosphonic acid; the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphinochloridites, $R_2PCl$, alkyl alkylphosphonochloridates, $(RO)(R)P(O)Cl$, and dialkyl phosphinochloridates, $R_2P(O)Cl$.

Preferred phosphorus-containing compounds include trimethylphosphite and phosphorus trichloride. In the trimethylphosphite, the covalent ionic constituent capable of reacting with hydrogen ion is $[CH_3—O—]^-$. In the phosphorus trichloride, the covalent or ionic constituent capable of reacting with hydrogen ion is $[—Cl]^-$.

After contact of the boron oxide and/or magnesium oxide-containing zeolite with the phosphorus reagent, the resulting composite is dried and heated in a manner similar to that used in preparing the boron oxide and/or magnesium oxide-containing zeolite.

Alternatively, the boron and phosphorus or magnesium and phosphorus or phosphorus and boron reagents, or other combinations, may be premixed in the desired ratios and the mixture or solution applied to the catalyst by the techniques described previously.

In practicing the desired conversion process, it may be desirable to incorporate the modified zeolite in another material resistant to the temperature and other conditions employed in the process. Such matrix material include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or other in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

The process of this invention is conducted such that alcohol and/or ether conversion is carried out in the vapor phase by contact in a reaction zone, such as for example, a fixed bed of catalyst, under effective conversion conditions, said catalyst being characterized as above-defined and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions.

The alcohol and/or ether conversion process described herein may be carried out as a batch-type, semi-continuous or continuous operation utilizing a fixed or moving bed catalyst system. A preferred embodiment entails use of a catalyst zone wherein the alcohol or ether charge is passed concurrently or countercurrently through a moving bed of particle-form catalyst. The latter after use is conducted to a regeneration zone wherein coke is burned from the catalyst in an oxygen-containing atmosphere, e.g. air, at an elevated temperature, after which the regenerated catalyst is recycled to the conversion zone for further contact with the alcohol and/or ether feed.

The product stream in the process of this invention contains steam and a hydrocarbon mixture particularly rich in light olefins, ethylene and propylene and aromatic hydrocarbons. Generally, a major fraction of the total olefins calculated on a mol basis, is ethylene plus propylene; and a major fraction of these two olefins is ethylene. When the conditions of reaction are adjusted to produce a higher proportion of liquid hydrocarbon products i.e. higher temperature, the predominant aromatic hydrocarbons are monocyclic hydrocarbons such as benzene, toluene and xylenes. Thus, the predominant hydrocarbons are all valuable petrochemicals. The steam and hydrocarbons are separated from one another by methods well known in the art. The particular proportions of olefins and aromatic hydrocarbons that are produced may be varied by varying the ratio of metal oxide to crystalline aluminosilicate, higher metal oxide contents favoring olefin formation. The proportions also may be varied by selecting reaction conditions within the ranges specified above, olefin production being favored by lower temperatures and in general by less severe conversion conditions. Thus, it is a feature of this invention that the product mix can be easily varied to suit changes of demand.

The following examples will serve to illustrate the process of the invention without limiting the same:

EXAMPLE 1

10.2 gram sample of $NH_4$ ZSM-5 having a crystal size of 0.02–0.05 micron was suspended in a solution of 11.67 grams of magnesium acetate [$Mg(OAc)_2$, 4 $H_2O$] in 25 milliliters of water at about 60° C for 18 hours. The slurry was poured into a crystallizing dish and placed in an oven at 110° C. As the water evaporated, the slurry was stirred frequently. When a powder was formed, the temperature was increased to 200° C and held for about 2 hours. It was then placed in a 500° C furnace, in air, in an open dish for about 17 hours to yield 11.9 grams of modified catalyst with 11.4 weight percent magnesium present as the oxide.

A 5 gram sample of the resulting catalyst was employed to convert methanol to hydrocarbons. The conditions of reaction and results are set forth in Table III below:

TABLE III

| Run No. | 1 | 2 | 3 | 4 | 5 |
|---|---|---|---|---|---|
| Temp, °C | 300 | 350 | 395 | 400 | 450 |
| WHSV | 3.1 | 3.1 | 3.2 | 3.1 | 3.2 |
| MeOH Conv. Total | 20.0 | 74.5 | 83.6 | 99.8 | 99.5 |
| Total Hydrocarbons | 4.6 | 5.3 | 30.9 | 40.6 | 39.3 |
| % para in Xylene Prod. | — | — | 93.9 | 81.5 | 94.5 |
| Selectivity to Products, Wt. % | | | | | |
| Benzene | 0 | 0 | 1.2 | .9 | 1.0 |
| Toluene | 0 | 0 | 1.1 | 1.7 | 1.0 |
| Ethylbenzene | 0 | 0 | .2 | .2 | .2 |
| p-Xylene | 0 | 0 | 4.1 | 6.9 | 7.7 |
| m-Xylene | 0 | 0 | .2 | .4 | .4 |
| o-Xylene | 0 | 0 | 0 | 1.2 | .1 |
| Higher Aromatics | 0 | 0 | 1.8 | 2.8 | 2.9 |
| Total Aromatics | 0 | 0 | 8.6 | 14.1 | 13.3 |
| $CO + CO_2$ | .4.1 | .8 | .3 | .8 | .3 |
| $CH_4$ | 20.5 | 4.6 | 1.8 | 2.4 | 2.0 |
| $C_2H_6 + C_3H_8$ | 1.9 | .9 | 1.5 | 2.6 | 2.0 |
| $C_2H_4$ | 61.5 | 48.7 | 26.0 | 17.2 | 15.3 |
| $C_3H_6$ | 9.9 | 20.0 | 25.2 | 15.7 | 15.2 |
| $C_4$. | 2.1 | 1.3 | 3.2 | 3.9 | 3.5 |
| $C_4=$ | 0 | 13.7 | 13.6 | 17.8 | 18.8 |
| $C_5^+$ | 0 | 10.0 | 19.8 | 25.5 | 29.6 |
| TOTAL | 100.0 | 100.0 | 100.0 | 100.0 | 100.0 |
| Run No. | 6 | 7 | 8 | 9 | 10 |
| Temp, °C | 500 | 550 | 600 | 350 | 400 |
| WHSV | 3.1 | 3.2 | 3.1 | 1.4 | 1.5 |
| MeOH Conv. Total | 100 | 100 | 100 | 81.7 | 96.9 |
| Total Hydrocarbons | 37.5 | 39.0 | 42.1 | 13.9 | 39.8 |

TABLE III-continued

| | | | | | |
|---|---|---|---|---|---|
| % para in Xylene Prod. | 91.7 | 90.0 | 86.2 | — | 92.6 |
| Selectivity to Products, Wt. % | | | | | |
| Benzene | .4 | .2 | 0 | 0 | 1.7 |
| Toluene | 2.1 | 2.0 | 2.2 | 0 | 2.3 |
| Ethylbenzene | .6 | .3 | 0 | 0 | 2.0 |
| p-Xylene | 6.5 | 5.7 | 5.1 | 0 | 10.7 |
| m-Xylene | .4 | .5 | .6 | 0 | .7 |
| o-Xylene | .1 | .2 | .2 | 0 | .2 |
| Higher Aromatics | 2.6 | 1.7 | 1.9 | 0 | 1.2 |
| Total Aromatics | 12.7 | 10.6 | 10.0 | 0 | 18.8 |
| $CO + CO_2$ | .4 | .8 | 5.5 | 1.3 | .1 |
| $CH_4$ | 2.8 | 7.3 | 23.3 | 2.8 | .5 |
| $C_2H_6 + C_3H_8$ | 2.3 | 2.5 | 2.3 | 1.1 | 2.9 |
| $C_2H_4$ | 19.3 | 15.4 | 19.9 | 50.3 | 12.6 |
| $C_3H_6$ | 19.3 | 27.1 | 22.0 | 27.5 | 18.9 |
| $C_4$· | 3.1 | 2.5 | 1.0 | 1.6 | 6.3 |
| $C_4=$ | 20.2 | 19.9 | 11.2 | 9.7 | 18.1 |
| $C_5+$ | 19.9 | 13.9 | 4.8 | 5.7 | 21.8 |
| TOTAL | 100.0 | 100.0 | 100.0 | 100.0 | 100.0 |

From the above results, it will be seen that light olefins, particularly ethylene and propylene, were major products along with up to 18 percent aromatics. The concentration of para-isomer in the xylene product fraction was exceptionally high compared with the normal equilibrium concentration of 24 percent.

EXAMPLE 2

In a manner similar to that described in Example 1, a sample of HZSM-5 was impregnated with magnesium acetate in aqueous solution to yield a modified catalyst which contained approximately 11.4 weight percent magnesium, in the form of magnesium oxide, after calcination in air.

A sample of this catalyst was tested for its ability to convert methanol to products at 415° C, atmospheric pressure and a WHSV of 3.4. The selectivity to hydrocarbons products in weight percent was as follows: Benzene, 1.33%; Toluene, 4.95%; Ethylbenzene, 0.53%; p-Xylene, 10.41%; o-Xylene, 0.06%; m-Xylene, 0.43%; other Aromatics, 4.49%; Carbon Monoxide, 0.15%; Methane, 158%; Ethane, 0.19%; Carbon Dioxide, 0.08%; Ethylene, 13.01%; Propane, 3.26%; Propylene, 12.96%; Butanes, 5.55%; Butenes, 9.17%; $C_5$ Aliphatics, 14.05%; $C_6$ Aliphatics, 11.89% and $C_7+$ Aliphatics, 5.89%. Methanol conversion was 97.2 percent.

It will be evident from the above results that the para-isomer accounted for 95.5 percent of the xylene product formed and that only a small amount of ethylbenzene was produced. Olefins predominated in the aliphatic product with ethylene and propylene being the major olefin products.

EXAMPLE 3

A 20 gram sample of microcrystalline $NH_4$ ZSM-5 (.02–0.5 micron crystal size) was suspended in a solution of 5.35 grams of boric acid in 40 milliliters of water at a temperature of 85°–87° C for a period of 15 hours. In a manner similar to that described in Example 1, the water was evaporated with stirring at 110°–200° C and calcined overnight at 500° C in air to yield a catalyst which contained about 4.1 weight percent boron, present as the oxide.

A 5.5 gram portion of the catalyst was placed in a crystallizing dish and 0.2214 gram of 85% $H_3PO_4$ dissolved in 6.5 milliliters of water was rapidly added stirring. A smooth viscous paste was formed which was immediately placed in an oven at 155° C and stirred frequently. The catalyst was converted to dry powder in about 25 minutes. The temperatures was increased to 200° C and the catalyst held for about 4 hours at this temperature. It was then placed in a 500° C furnace, in air, for 3.5 hours. The resulting catalyst contained approximately 4 weight percent of boron and 1 weight percent of phosphorus, both being present as the oxide after calcination at 500° C.

A sample of this catalyst was tested for its ability to convert methanol to hydrocarbons. The selectivity to hydrocarbon products and conditions of reaction are shown in Table IV below:

TABLE IV

| Run No. | 1 | 2 |
|---|---|---|
| Temp. ° C | 300 | 400 |
| WHSV, Hr | 3.0 | 3.1 |
| MeOH Conv, Total % | | |
| to Hydrocarbons | 31.5 | 39.8 |
| % para in Xylene Product | 97.3 | 98.7 |
| Selectivity to Products | | |
| Wt. % | | |
| Benzene | .16 | .38 |
| Toluene | 1.32 | 1.07 |
| p-Xylene | 4.35 | 5.25 |
| m-Xylene | .10 | .06 |
| o-Xylene | .02 | .01 |
| Higher Aromatics | 1.71 | 1.55 |
| TOTAL AROMATICS | 7.65 | 8.32 |
| $CO + CO_2$ | .21 | .11 |
| $CH_4$ | 1.20 | 1.32 |
| $C_2H_6 + C_3H_8$ | 2.71 | 4.92 |
| $C_2H_4$ | 30.87 | 29.42 |
| $C_3H_6$ | 26.01 | 22.13 |
| $C_4$ Paraffins | 3.27 | 6.72 |
| $C_4$ Olefins | 16.41 | 15.54 |
| $C_5+$ | 11.67 | 11.52 |
| TOTAL | 100.0 | 100.0 |

From the above results, it will be evident that a very substantial increase in the amount of para-isomer in the xylene product was observed over the thermodynamic equilibrium value. In addition, it will be seen that substantial quantities of light olefins, particularly ethylene and propylene, were produced.

EXAMPLE 4

In a manner similar to that described in Example 1, 20 grams of microcrystalline ammonium ZSM-5 was suspended in a solution of 4.28 grams of ortho boric acid in 50 milliliters of water at approximately 80° C. After standing overnight and transferring the entire slurry to a dish, evaporation of the water with stirring, heating to 200° C, the catalyst was finally placed in an oven at 500° C in air overnight. A catalyst product in an amount of 20.99 grams having a boron oxide content of 3.34 weight percent was obtained.

A 5 gram sample of 8–12 mesh particles of this catalyst was tested for its ability to convert methanol to products. The temperature of the catalyst bed was 500°

C. The weight hourly space velocity of the methanol feed was approximately 3.6 The duration of the run was approximately 1 hour.

Analysis of the products showed that 100 percent of the methanol had been converted. Of the hydrocarbon products, approximately 36 percent were aromatics, 57 percent were light gases and 7 percent $C_5+$ aliphatic products. The aromatic portion contained 48.7 percent xylene. In the xylene fraction, 82.3 percent was the para-isomer, 13.5 percent was the meta-isomer and 4.2 percent was the ortho-isomer.

It will be evident that a high proportion of the xylene fraction was converted to the para-isomer.

EXAMPLE 5

Methanol was passed over the catalyst described in Example 4 at a temperature of 400° C and a weight hourly space velocity of about 3.

Analysis of the products showed that 93 percent of the methanol was converted. The composition of the conversion products was approximately 17 percent aromatics, 50 percent light gases ($C_1$–$C_3$) and 33 percent $C_4+$ aliphatic compounds. The aromatic portion contained 59 percent xylenes with 84 percent of such xylenes being the para-isomer.

EXAMPLE 6

In a manner similar to that described in Example 1, 10.0 grams of HZSM-5 zeolite was suspended in a solution of 0.56 gram of 85% phosphoric acid and 11.67 grams of magnesium acetate tetrahydrate in 25 ml. of water at about 90° C. The slurry was allowed to stand at this temperature for about 16.5 hours. After evaporation of the water, heating to 200° C and then 500° C overnight, a 5 gram sample of the catalyst was evaluated for its ability to convert methanol to hydrocarbons. The various conditions of reaction and results are summarized in Table V.

TABLE V

| Run No. | 1 | 2 | 3 | 4 |
|---|---|---|---|---|
| Temp, ° C | 300 | 350 | 400 | 450 |
| WHSV | 3.1 | 3.3 | 3.1 | 3.2 |
| Conv. to Hydrocarbons, % | 2.7 | 3.4 | 35.3 | 43.2 |
| % para in Xylene Product | — | — | 98.1 | 97.5 |
| Selectivity to Products, Wt. % | | | | |
| Benzene | 0 | 0 | 1.3 | .7 |
| Toluene | 0 | 0 | 2.2 | 1.7 |
| Ethylbenzene | 0 | 0 | .9 | .5 |
| p-Xylene | 0 | 0 | 9.8 | 6.4 |
| m-Xylene | 0 | 0 | .2 | .1 |
| o-Xylene | 0 | 0 | 0 | .1 |
| Higher Aromatics | 0 | 0 | 3.0 | 1.8 |
| Total Aromatics | 0 | 0 | 17.4 | 11.3 |
| $CO + CO_2$ | 0 | 1.4 | .2 | .3 |
| $CH_4$ | 12.3 | 1.1 | 1.4 | 1.6 |
| $C_2H_6 + C_3H_8$ | .1 | 1.9 | 2.2 | 2.4 |
| $C_2H_4$ | 69.0 | 56.5 | 22.5 | 14.1 |
| $C_3H_6$ | 18.3 | 31.4 | 21.8 | 26.1 |
| $C_4$· | 0 | 1.4 | 3.7 | .4 |
| $C_4=$ | .3 | 6.3 | 13.3 | 16.4 |
| $C_5+$ | 0 | 0 | 17.5 | 27.4 |
| TOTAL | 100.0 | 100.0 | 100.0 | 100.0 |

It can be seen that high selectivities to light olefins, especially ethylene, were observed at the lower temperatures of operation. At the higher temperature of operation, a combination of $C_2$ to $C_4$ olefins and aromatics were the major products. In the xylene fraction of the aromatic product, the concentration of the para isomer was exceptionally high (97+%) by comparison with that found in the equilibrium mixture (24%).

EXAMPLE 7

In a manner similar to that described in Example 6, boric acid and magnesium acetate were used to impregnate HZSM-5 zeolite to give a catalyst after calcination with air that contained approximately 10.5 weight percent magnesium and 0.9% boron. A five gram sample of the catalyst was evaluated for its ability to convert methanol to hydrocarbons. The various conditions of reaction and results are summarized in Table VI.

TABLE VI

| Run No. | 1 | 2 | 3 | 4 | 5 | 6 |
|---|---|---|---|---|---|---|
| Temp, ° C | 300 | 350 | 350$^{(a)}$ | 400 | 450 | 400 |
| WHSV | 3.1 | 3.2 | 3.2 | 3.1 | 3.1 | 1.6 |
| Conv. to Hydrocarbons | 2.1 | 1.8 | 2.8 | 9.9 | 27.2 | 13.3 |
| % para in Xylene Product | — | — | — | — | 95.8 | — |
| Selectivity to Products, Wt. % | | | | | | |
| Benzene | 0 | 0 | 0 | 0 | 1.0 | 0 |
| Toluene | 0 | 0 | 0 | 0 | 1.6 | 0 |
| Ethylbenzene | 0 | 0 | 0 | 0 | .6 | 0 |
| p-Xylene | 0 | 0 | 0 | 0 | 4.8 | 0 |
| m-Xylene | 0 | 0 | 0 | 0 | .2 | 0 |
| o-Xylene | 0 | 0 | 0 | 0 | 0 | 0 |
| Higher Aromatics | 0 | 0 | 0 | 0 | 1.6 | 0 |
| Total Aromatics | 0 | 0 | 0 | 0 | 9.8 | 0 |
| $CO + CO_2$ | 0 | 12.4 | 22.1 | 1.6 | .5 | 3.0 |
| $CH_4$ | 8.7 | 18.0 | 24.6 | 3.1 | 2.1 | 4.6 |
| $C_2H_6 + C_3H_8$ | 4.6 | 4.1 | 4.2 | .9 | .9 | .9 |
| $C_2H_4$ | 21.0 | 40.3 | 39.4 | 56.4 | 20.1 | 47.0 |
| $C_3H_6$ | 45.1 | 16.6 | 9.1 | 29.4 | 29.3 | 31.0 |
| $C_4$· | 6.2 | 1.0 | .1 | .8 | 2.2 | 2.1 |
| $C_4=$ | 14.4 | 6.3 | .5 | 7.8 | 13.7 | 11.4 |
| $C_5+$ | 0 | 1.3 | 0 | 0 | 21.4 | 0 |
| TOTAL | 100.0 | 100.0 | 100.0 | 100.0 | 100.0 | 100.0 |

$^{(a)}$ Passed water vapor over catalyst at 500° C, WHSV = 3.5 for 30 minutes between runs 2 and 3.

It will be seen that high selectivities to light olefins, especially ethylene, were observed at the lower temperatures. In other cases, exceptionally high selectivities to light olefins, $C_2$–$C_4$, exceeding 80% selectivity to hydrocarbon products were observed. In the run at 450° C, the concentration of the p-isomer in the xylene product was 95.8%.

EXAMPLE 8

The same catalyst was used as in Example 6. An analysis of the products where methanol was used as the feed has indicated that an equilibrium is very rapidly established between 2 moles of methanol and a mole each of dimethyl ether and water. In this example, dimethyl ether was used as the feed. It will form an equilibrium mixture which will have a significantly smaller amount of water and methanol present in the catalyst bed. The results using 5 grams of catalyst with dimethyl ether as the feed are summarized in Table VII.

TABLE VII

| Run No. | 1 | 2 | 3 |
|---|---|---|---|
| Temp, °C | 300 | 350 | 350 |
| WHSV | 1.2 | 1.2 | 2.5 |
| Conv to Hydrocarbons, % | 38.8 | 51.1 | 34.4 |
| % para in Xylene Product | 86.1 | 95.7 | 94.7 |
| Selectivity to Products, Wt. % | | | |
| Benzene | .1 | 1.4 | .8 |
| Toluene | .7 | 2.1 | .9 |
| Ethylbenzene | .1 | .1 | .1 |
| p-Xylene | 1.4 | 8.9 | 3.4 |
| m-Xylene | .2 | .3 | .2 |
| o-Xylene | .1 | .1 | 0 |
| Higher Aromatics | .9 | 4.1 | 1.8 |
| Total Aromatics | 3.5 | 17.0 | 7.2 |
| CO + $CO_2$ | .7 | .2 | .1 |
| $CH_4$ | 3.2 | 1.8 | 1.4 |
| $C_2H_6$ + $C_3H_8$ | 2.9 | 4.7 | 2.1 |
| $C_2H_4$ | 48.3 | 26.1 | 32.3 |
| $C_3H_6$ | 23.1 | 15.7 | 28.5 |
| $C_4$- | 2.7 | 4.4 | 3.3 |
| $C_4$= | 10.2 | 12.8 | 14.5 |
| $C_5$+ | 5.4 | 17.3 | 10.6 |
| TOTAL | 100.0 | 100.0 | 100.0 |

It can be seen that light olefins, especially ethylene, are major products and that the para-isomer is present as a major component in the xylene product.

EXAMPLE 9

In a manner similar to that described in Example 1, 6.0 grams of HZSM-11 was impregnated with 7.0 grams of magnesium acetate tetrahydrate dissolved in 15 ml. of water to give a catalyst which contained approximately 11.1 wt.% magnesium after heating, in air, for 16 hours. A 5 gram sample of this catalyst was tested for its ability to convert dimethylether to products. The conditions of reaction and results are summarized in Table VIII.

TABLE VIII

| | |
|---|---|
| Temp, °C | 300 |
| WHSV | 1.2 |
| Conv. to Hydrocarbons | 42.1 |
| % para in Xylene Product | 62.7 |
| Selectivity to Products, Wt. % | |
| Benzene | 1.3 |
| Toluene | 1.7 |
| Ethylbenzene | .4 |
| p-Xylene | 3.7 |
| m-Xylene | 2.0 |
| o-Xylene | .2 |
| Higher Aromatics | 6.4 |
| Total Aromatics | 15.7 |
| CO + $CO_2$ | 3.7 |
| $CH_4$ | 2.2 |
| $C_2H_6$ + $C_3H_8$ | .9 |
| $C_2H_4$ | 36.0 |
| $C_3H_6$ | 16.8 |
| $C_4$- | 4.1 |
| $C_4$= | 10.6 |
| $C_5$+ | 10.0 |
| TOTAL | 100.0 |

It can be seen that relatively large amounts of light olefins, especially ethylene, were produced and that the concentration of the para-isomer in the xylene product was significantly higher than the equilibrium value.

I claim:

1. A catalyst composition comprising a crystalline aluminosilicate zeolite, said zeolite having a silica to alumina ratio of at least about 12, a constraint index within the approximate range of 1 to 12, and having combined therewith:
    1. between about 0.25 and about 25 percent by weight of boron oxide; or
    2. between about 0.25 and about 5 percent by weight of boron oxide in combination with between about 2 and about 15 percent by weight of magnesium oxide; or
    3. between about 0.25 and about 10 percent by weight of phosphorus oxide in combination with between about 0.25 and about 25 percent by weight of boron oxide or magnesium oxide, or
    4. between about 0.25 and about 10 percent by weight of phosphorus oxide in combination with between about 0.25 and about 5 percent by weight of boron oxide and between about 2 and about 15 percent by weight of magnesium oxide.

2. The catalyst composition of claim 1 wherein said crystalline aluminosilicate zeolite is ZSM-5.

3. The catalyst composition of claim 2 wherein ZSM-5 is predominately in the hydrogen form.

4. The catalyst composition of claim 1 wherein said crystalline aluminosilicate zeolite is ZSM-11.

5. The catalyst composition of claim 4 wherein ZSM-11 is predominately in the hydrogen form.

6. The catalyst composition of claim 1 wherein said zeolite has combined therewith between about 0.25 and about 10 percent by weight of phosphorus oxide and between about 1 and about 15 percent by weight of magnesium oxide.

7. The catalyst composition of claim 1 wherein said zeolite has combined therewith between about 1 and about 15 percent by weight of a oxide of boron and between about 0.25 and about 10 percent by weight of phosphorus oxide.

8. The catalyst composition of claim 1 wherein said zeolite has combined therewith between about .25 and about 15 percent by weight of boron oxide.

9. The catalyst composition of claim 1 wherein said zeolite has combined therewith between about 0.5 and about 5 percent by weight of phosphorus oxide in combination with between about 0.25 and about 25 percent by weight of boron oxide or magnesium oxide.

10. The catalyst composition of claim 1 wherein said zeolite has combined therewith an oxide of phosphorus in an amount of between about 0.5 and about 5 weight percent in combination with between about 0.25 and about 5 percent by weight of boron oxide and between about 2 and about 15 percent by weight of magnesium oxide.

* * * * *

UNITED STATES PATENT AND TRADEMARK OFFICE
CERTIFICATE OF CORRECTION

PATENT NO. : 4,049,573
DATED : September 20, 1977
INVENTOR(S) : WARREN W. KAEDING It is certified that error appears in the above-identified patent and that said Letters Patent are hereby corrected as shown below:

Column 13, line 38          "158%" should be ---1.58%---

Signed and Sealed this

Second Day of May 1978

[SEAL]

Attest:

RUTH C. MASON
Attesting Officer

LUTRELLE F. PARKER
Acting Commissioner of Patents and Trademarks